United States Patent
Chynn (12)

(10) Patent No.: US 6,218,428 B1
(45) Date of Patent: Apr. 17, 2001

(54) OPHTHALMIC COMPOSITION

(76) Inventor: Emil Chynn, 101 W. 12th St., Apt. 18-C, New York, NY (US) 10011

( * ) Notice: Subject to any disclaimer, the term of this patent is extended or adjusted under 35 U.S.C. 154(b) by 0 days.

(21) Appl. No.: 09/561,465

(22) Filed: Apr. 28, 2000

(51) Int. Cl.$^7$ .............................. A61K 31/35; A61K 3/24
(52) U.S. Cl. .......................... 514/459; 514/540; 514/912
(58) Field of Search ................................... 514/540, 459, 514/912

(56) References Cited

U.S. PATENT DOCUMENTS

| | | |
|---|---|---|
| 3,306,820 | 2/1967 | Krezanoski . |
| 5,610,184 | 3/1997 | Shahinian, Jr. ...................... 514/540 |
| 5,760,077 | 6/1998 | Shahinian, Jr. ...................... 514/540 |
| 5,795,912 | 8/1998 | Tsubota ............................... 514/458 |
| 5,795,913 | 8/1998 | Lahmussaari et al. .............. 514/459 |

FOREIGN PATENT DOCUMENTS

| | | |
|---|---|---|
| 835940 | 3/1970 | (CA) . |

OTHER PUBLICATIONS

Apt et al., Apr. 1980, Pupillary dilation with single eyedrop mydriatic combinations, *Am. J. Ophthalmol.* 89:553–559.

Brady et al, May–Jun. 1994, Dilution of proparacaine in balanced salt solution reduces pain of anesthetic instillation in the eye, *Regional Anesthesia* 19(3):196–8 (Abstract only).

Cabrera et al., Apr. 1998, Changes in intraocular pressure due to cycloplegia, *CLAO Journal* 24(2):111–114.

Cooper et al., Nov. 1996, Pupillary dilation and funduscopy with 1.0% hydroxyamphetamine plus 0.25% tropicamide (Paremyd) versus tropicamide (0.5 to 1.0%) as a function of iris and skin pigmentation, and age, *Journal of the American Optometric Association* 67(11):669–75 (Abstract only).

Elibol et al., Apr. 1997, The influence of drop size cyclopentolate, phenylephrine and tropicamide on pupil dilation and systemic side effects in infants, *Acta Ophthalmologica Scandinavica* 75(2):178–80 (Abstract only).

Eyeson–Annan et al., Apr. 1998, Comparative pupil dilation using phenylephrine alone or in combination with tropicamide, *Ophthalmology* 105(4):726–732.

Holtz, Aug. 1975, Clinical Study of the Safety of a Fluorescein–Anesthetic Solution, *Annals of Ophthalmology* pp. 1101–1102.

Larkin et al., 1989, Ideal concentration of tropicamide with hydroxyamphetamine 1% for routine pupillary dilation, *Ann. Ophthalmol.* 21:340–344.

Lee et al., May 1999, Formulation and in vivo evaluation of ocular insert containing phyenylephrine and tropicamide, *International Journal of Phamaceutics* 182 (1):121–6 (Abstract only).

Liu et al., May 1993, Topical bupivacaine and proparacaine: a comparison of toxicity, onset of action, and duration of action, *Cornea* 12(3):228–32 (Abstract only).

Lovasik et al., May 1990, Time course of cycloplegia induced by a new phenylephrine–tropicamide combination drop, *Optometry & Vision Science* 67(5):352–358.

Maus et al., Feb. 1999, Measurement of aqueous humor flow by fluorophotometry in the presence of a dilated pupil, *Investigative Ophthalmoloy & Visual Science* 40(2):542–6 (Abstract only).

Nagataki et al., 1979, Pharmacokinetics of Instilled Drugs in the Human Eye, pp:33–49.

Quickert, Jun. 1967, A fluorescein–Anesthetic Solution for Applanation Tonometry, *Arch Ophthal* 77:734–739.

Bright et al., D.C., 1981, Goldman applanation tonometry without fluorescein, American Journal of Optometry & Physiological Optics 58(12):1120–1126.

Levine, Jul., 1982, Mydriatic effectiveness of dilute combinations of phenylephrine and tropicamide, American Journal of Optometry & Physiological Optics 59(7):580–94.

Ramselaar, Sep. 1988, Corneal epithelial permeability after instillation of ophthalmic solutions containing local anaesthetics and preservatives, *Current Eye Research* 7(9):947–50.

Sasaki et al., Sep. 1995, Ophthalmic preservatives as absorption promotors for ocular drug delivery, *Journal of Pharmacy & Pharmacology* 47(9):703–707.

Siderov et al., Dec. 1997, Effect of proparacaine on tropicamide–induced mydriasis, *Optometry & Vision Science* 74(12):1039–1043.

Tanner et al., 1996, A comparative study of the efficacy of 2.5% phenylephrine and 10% phenylephrine in pre–operative mydriasis for routine cataract surgery, *Eye* 10(Pt. 1):95–8.

Wolfs et al., Nov. 1997, Risk of acute angle–closure glaucoma after diagnostic mydriasis in nonselected subjecs: the Rotterdam Study, *Investigative Ophthalmology & Visual Science* 38(12):2683–7 (Abstract only).

(List continued on next page.)

*Primary Examiner*—Zohreh Fay
(74) *Attorney, Agent, or Firm*—Pennie & Edmonds LLP

(57) ABSTRACT

The current invention is an ophthalmic composition that combines multiple agents necessary to perform a routine eye examination. Preferably, the composition is a mixture of a topical local anesthetic, a pupillary dilating agent, and a dye, all in solution. The composition may also include a preservative, a wetting agent, a diluting agent, and/or a buffer. The preferred composition provides a means to: 1) anesthetize the cornea to allow for pain relief, manipulation and the measurement of intraocular pressure, 2) dye the cornea and conjunctiva to allow for the detection of pathology and for the measurement of intraocular pressure, and 3) dilate the pupil to allow for examination of the optic nerve, macula, retina, retinal vasculature, and peripheral fundus. In addition, the invention includes a method of using the inventive composition and a method of using currently available compositions that allow for a more rapid eye examination by eliminating or reducing a waiting period that follows the administration of dilating agents according to the present state of the art. Moreover, the inventive composition may be used pre-operatively before ophthalmic surgery, thereby conferring many of the same advantages as described above.

29 Claims, No Drawings

OTHER PUBLICATIONS

Zeise et al., Nov. 1996, Comparison of efficacy and tolerance between 1% hydroxyamphetamine plus 0.25% tropicamide (Paremyd) and 0.5% tropicamide combined with 2.5% phenylephrine *Journal of the American Optometric Association* 67(11):681–9 (Abstract only).

Package insert for Ak–Dilate™ solution, Phenylephrine Hydrochloride Ophthalmic Solution, USP 2.5%–Sterile, dated Jan., 1998, sold by Akorn, Inc.

Package insert for Tropicamide Ophthalmic Solution,USP, dated Dec., 1996, sold by Bausch & Lomb Pharmaceuticals, Inc.

Package insert for Fluress® solution, Fluorescein Sodium and Benoxinate Hydrochloride Opthalmic Solution, USP Sterile, dated Sep., 1997, sold by Akoon, Inc.

Package insert for Fluoracaine® solution, Fluorescein Sodium and Proparacaine Hydrochloride Ophthalmic Solution, USP Sterile, dated Dec., 1997, sold by Akorn, Inc.

Package insert for Ak–Fluor® solution, Fluorescein Injection, USP 10% and 25% Sterile Solution, dated Mar., 1995, sold by Akorn, Inc.

Package insert for Alcaine® solution, Proparacaine hydrochloride ophthalmic solution, USP 0.5%, sold by Alcon.

Package insert for Mydriacyl® solution, Tropicamide ophthalmic solution, USP, dated Feb., 1997, sold by Alcon (Puerto Rico) Inc.

Package insert for Phenylephrine Hydrochloride Ophthalmic Solution, Sterile ophthalmic solution, USP 2.5%, dated Dec., 1996, sold by Bausch & Lomb Pharmaceuticals, Inc.

Package insert for Fluorescein Sodium and Benoxinate Hydrochloride Ophthalmic Solution, Sterile ophthalmic solution, USP .25%/.4%, dated Apr., 1997, sold by bausch & Lomb Pharmaceuticals, Inc.

US 6,218,428 B1

OPHTHALMIC COMPOSITION

BACKGROUND OF THE INVENTION

1. Field of the Invention

The present invention relates to diagnostic ophthalmic compositions and a method of administering those compositions during routine eye examinations. In particular, the inventive compositions, which preferably contain a local anesthetic, a dye and a dilating agent, perform multiple functions, including: 1) anesthetizing the cornea to allow for pain relief, manipulation and the measurement of intraocular pressure ("IOP"), 2) dying the cornea to allow for the detection of pathology and the measurement of IOP, and 3) dilating the pupil to allow for examination of the optic nerve, macula, retina, retinal vasculature, and peripheral fundus ("dilated exam"). These compositions may also include a preservative, a wetting agent, a diluting agent, and/or buffers. The method of administering these ophthalmic compositions enables the physician to perform more efficient eye examinations. The compositions may also be used to perform similar functions prior to ophthalmic surgery.

2. Background

A routine eye examination typically consists of three basic components: 1) examination of the front structures of the eye; 2) measurement of IOP; and 3) examination of the optic nerve, macula, retina, retinal vasculature, and peripheral fundus (the "dilated fundus exam"). The current state of the art consists of sequentially administering multiple topical agents to a patient's eye in order to perform the multiple components of the examination. This sequence is described as follows:

First, a topical anesthetic agent, usually proparacaine or tetracaine, is applied to the eyes to anesthetize the cornea and allow for visualization and manipulation. Next, a fluorescein strip (or other acceptable dye) is applied to the tear film as a disclosing agent to reveal pathology, such as corneal abrasions or ulcers. The application of topical anesthesia and fluorescein is followed by the measurement of IOP by applanation tonometry, which is the method most commonly used by clinicians to measure IOP. After the cornea is examined and IOP is measured, a topical dilatipg agent is usually instilled to dilate the pupil, thereby permitting dilated fundus exam by direct and/or indirect ophthalmoscopy. The dilating agents used are typically sympathomemetic agents, parasympatholytic agents, or both. After instilling the dilating agent(s), the doctor and patient must wait approximately twenty minutes to allow for adequate pupillary dilation in order to conduct the dilated fundus exam (the "waiting time"). The waiting time is an extremely inefficient part of the routine eye examination according to the current state of the art.

Diagnostic ophthalmic compositions currently exist which combine some, but not all, of the above components to allow for some, but not all, of the necessary functions for a complete eye exam. For example, a combination of benoxinate hydrochloride (a topical anesthetic agent) and fluorescein sodium (a dye) is currently available (by Akom, Inc., of Decatur, Ill.). This combination provides anesthesia to the patient's eye and simultaneously stains the cornea to allow for corneal examination and IOP measurement. Another currently available combination anesthetic/dye is FLUORACAINE® solution, also by Akom, Inc. This combination agent includes proparacaine hydrochloride as the anesthetic and fluorescein sodium as the dye. However, even with the use of these currently available combination agents, after measuring IOP, according to the current state of the art, the doctor must still apply one or more dilating agents and allow for the waiting time to elapse before performing a dilated fundus examination.

Other formerly available combination agents combine two dilating agents, specifically a sympathomemetic agent and a parasympatholytic agent. For example, a combination of phenylephrine and tropicamide, and a combination of tropicamide and hydroxyamphetamine were formerly available. Notwithstanding all of the above-mentioned commercially available combination agents, at least two distinct compositions are required according to the current state of the art for a complete eye examination—a combination anesthetic-dye drop applied before IOP measurement, and a dilating agent or combination dilating agent applied after IOP measurement. Thus, with the current state of the art, multiple drops are still required and the inefficient waiting time is still a necessary part of the examination to allow for sufficient pupillary dilation. It would be advantageous to eliminate the multiple eye drops necessary for a complete eye examination, as well as provide a method of administration which eliminates or greatly reduces the waiting time, thereby maximizing efficiency and minimizing patent discomfort.

SUMMARY OF THE INVENTION

The present invention relates to diagnostic ophthalmic compositions that contain various agents necessary to perform an eye examination. Preferably, the composition includes a topical local anesthetic, a dilating agent, and a dye. The composition may also include a preservative, a wetting agent, a diluting agent, and/or a buffer. The composition provides a means to: 1) anesthetize the front structures of the eye, allowing for their examination and manipulation, 2) dye the cornea and conjunctiva, allowing for the detection of pathology, 3) accurately measure IOP, and 4) dilate the pupil for dilated fundus exam. In addition, the method of administering the inventive composition allows for a more rapid and efficient eye examination because the waiting period necessary according to the present state of the art can be greatly reduced and, in most cases, even eliminated.

Using the composition, a complete eye examination may often be performed after instilling a single composition at the beginning of the examination. The composition thus saves time and cost, while minimizing patient discomfort and the inventory needed for conducting eye examinations. Alternatively, the various components that comprise the inventive composition can be administered separately or in different combinations, all before measuring IOP, resulting in many of the same advantages as administering a single combination composition.

An embodiment of the inventive composition may also be used preoperatively before ophthalmic surgery (e.g., cataract surgery). In this regard, the composition will anesthetize the eye and provide for rapid and complete dilation. It has the added benefit of dying the eye to mark it for the operation to help prevent inadvertent surgery on a healthy fellow eye.

DETAILED DESCRIPTION OF THE INVENTION

A. Composition Components

One embodiment of the current invention is an ophthalmic composition that contains multiple agents necessary to perform a complete eye examination, often with a single instillation of the composition at the beginning of the examination. Preferably, the composition includes a local anesthetic, a dye, and a dilating agent. The composition may also include a preservative, a wetting agent, and a diluting agent. Administering the composition performs many of the functions necessary for a complete eye exam, including: 1) anesthetizing the front structures of the eye, allowing for their examination and manipulation, 2) dying the cornea and conjunctiva with a dye, allowing for the detection of pathology, 3) allowing accurate IOP measurement, and 4) dilating the pupil for dilated fundus eye exam.

The composition should contain a diagnostically acceptable amount of each desired component. A diagnostically acceptable amount is an amount that will perform the necessary function within the context of the eye examination and not cause undue interference or side effects that render the composition ineffective or unduly problematic for use in an eye examination. Routine tests, such as the clinical studies described in more detail hereinafter, and other tests and studies known to those skilled in the art will help determine the proper amounts and concentrations of each component. When describing a specific amount of each component, the concentrations of the components are expressed in terms of mg/ml when in solution.

The local anesthetic is used to anesthetize the front structures of the eye, allowing for their examination and manipulation without discomfort to the patient. Examples of useful anesthetics include proparacaine, tetracaine, lidocaine, procaine, hexylcaine, cocaine, bupivicaine, benoxinate, mepivacaine, prilocaine, etidocaine, benzocaine, chloroprocaine, propoxycaine, dyclonin, dibucaine, pramoxine, oxybuprocaine or other anesthetics useful for eye examinations. Preferably, the anesthetic should be in an amount between about 0.01% (or 0.01 mg/ml if in solution) and about 10% (or 10 mg/ml if in solution). More preferably, the anesthetic should be present in an amount between about 0.1% and about 5%. Most preferably, the anesthetic should be in an amount between about 0.1% and about 1% of the solution. Hereinafter, the concentration of each component is expressed in terms of a percentage. When the composition is in solution, the percentage is equivalent to mg/ml.

The dye is used to stain the cornea and conjunctiva so that corneal pathology can be detected. The dye is also useful to mark an eye prior to surgery on that eye to help ensure that the surgery is performed on the correct eye. Examples of useful dyes are fluorescein, rose bengal, lissamine green or other similar dyes. Preferably, the dye should be in an amount between about 0.01% and about 10%. More preferably, the dye should be present in an amount between about 0.05% and about 5%. Most preferably, the dye should be in an amount between about 0.1% and about 1% of the solution.

The dilating agent is used to dilate the pupils for examination of the posterior pole. Typically, these are sympathomemetic or parasympatholytic agent, or both, including phenylephrine, tropicamide, cyclopentolate, hydroxyamphetamine, atropine, homatropine and/or other dilating agents. Preferably, the total amount of dilating agent should be between about 0.01% and about 15%. More preferably, the total dilating agent should be present in an amount between about 0.1% and about 10%. Most preferably, the total dilating agent should be in an amount between about 0.1% and about 5% of the solution.

Examples of useful preservatives are benzalkonium chloride (preferably in a concentration of about 0.0001% to about 0.1%), chlorobutanol (preferably in a concentration of about 0.1% to about 10%), EDTA, methylparaben and propylparaben (parahydrobenzoic acid derivative), phenyl-ethyl alcohol (substituted alcohol), chlorhexidine, chlorobutanol, polyaminopropyl biguanide, polysorbate 20, or other preservatives as understood by those skilled in the art. Other than for benzalkonium chloride and chlorobutanol, the preservative is preferably in a concentration of about 0.0001% to about 10%, more preferably in a concentration of about 0.001% to about 1%, and most preferably in a concentration of about 0.01% to about 1%.

Examples of useful wetting agents are carboxymethylcellulose, hydroxypropyl methylcellulose, glycerin, mannitol, polyvinyl alcohol (PVA), hydroxyethylcellulose or other wetting agents as understood by those skilled in the art. Preferably, the wetting agent should be in an amount between 0.001% and 10%. More preferably, the wetting agent should be present in an amount between 0.01% and 5%. Most preferably, the wetting agent should be present in an amount between 0.1% and 1% of the solution.

Examples of diluting agents are water, distilled water, sterile water, artificial tears or other diluting agents as understood by those skilled in the art. Preferably, the diluting agent provides a substantial majority of the volume of the solution.

The invention may also contain a diagnostically acceptable amount of excipients, additives, and/or buffers. Buffers and other excipients are typically added to adjust the pH of the composition to make it acceptable to the eye and to maximize the efficiency of the components. Preferably, the pH of a composition instilled into the eye should be between about 4.0 to about 7.5. Excipients may include stabilizers and/or antioxidants to prevent drug degradation. Stabilizers may include sodium bisulfate or metabisulfate, preferably in a concentration ranging from about 0.01% to about 0.03%.

It should be understood that the list of ingredients above is merely a representative sampling of those that can be used with the present invention. Therefore, the scope of the present invention is not to be limited by the aforementioned examples. It may also be desired to provide an ophthalmic composition that combines some, but not all, of the aforementioned components. For example, diagnostically acceptable amounts of the anesthetic and dilating agent(s) can be combined (without the dye) or diagnostically acceptable amounts of the dye and the dilating agent(s) (without the anesthetic) can also be combined. Any of the other aforementioned components (e.g., preservative, wetting agents, diluting agent, excipients, buffers, etc.) can be added as well. The preferred amount of each component is as previously described. Any of the compositions within the scope of the present invention may be formulated as a solution, ointment, cream, suspension, gel, or sustained release vehicle.

The preferred composition is a solution mixture combining either 0.5% proparacaine hydrochloride, 0.5% tetracaine hydrochloride, or 0.4% benoxinate hydrochloride as the anesthetic, 0.25% fluorescein sodium as the dye, 2.5% phenylephrine hydrochloride and 1% tropicamide as the dilating agent(s), and a preservative, such as 1% chlorobutanol, 0.01% benzalkonium chloride, or other preservatives in an amount found in currently available agents. The preferred composition also includes a diagnostically acceptable concentrations of excipients, additives, wetting agents, diluting agents and/or buffers, such as those found in the components used to make an embodiment of the invention described below.

Some of the aforementioned components were used to make an embodiment of the invention for testing purposes (the "testing composition") in five clinical studies, as further described herein. These components were used because they were readily available on the market. The testing composition consists of: (1) fluorescein sodium and benoxinate hydrochloride as a 0.25% and 0.4% solution, respectively (by Akom Pharmaceuticals) (inactive ingredients: povidone, boric acid, purified water, sodium hydroxide and hydrochloric acid to adjust pH (pH 4.3–5.3); preservative: chlorobutanol 1%); (2) phenylephrine hydrochloride, sold by Akom Pharmaceuticals of Decatur, Ill., as a 10% solution (inactive ingredients: boric acid, sodium borate, sodium bisulfite, edetate disodium, purified water, and hydrochloric acid and/or sodium hydroxide to adjust pH (4.0–7.5); preservative: benzalkonium chloride 0.01%), and (3) tropicamide ophthalmic solution, sold by Bausch & Lomb Pharmaceuticals, Inc., as a 1% solution (inactive ingredients: boric acid, hydrochloric acid, edetate disodium, purified water, and sodium hydroxide and/or hydrochloric acid to adjust pH (4.0–5.8); preservative: benzalkonium chloride 0.01%).

The testing composition was prepared using a tuberculin syringe and a 30 g needle. From the components described above, 1.1 ml of the phenylephrine hydrochloride, 5.0 ml of the tropicamide, and 5.0 ml of the fluorescein/benoxinate solutions were drawn and combined to yield an ophthalmic composition consisting of phenylephrine hydrochloride 1.0%, tropicamide 0.45%, fluorescein sodium 0.11%, and benoxinate hydrochloride 0.18%. The testing composition was mixed by vigorous shaking before administration. A sterilized commercial dropper which yielded a drop size of approximately 30 microliters was used to instill drops of the composition into the patient's eyes.

B. Method of Administration and Proper Usage

The current invention includes a method of administering the preferred inventive composition and a method of administering some or all of the components of the inventive composition separately, rather than as a single combination agent. The following describes the method of using the inventive composition:

First, the clinician examines the anterior structures of the eye by slit-lamp ophthalnoscopy to ensure that the anterior chamber angle does not appear narrow, and therefore does not have an increased risk of induced angle closure upon pupillary dilation. According to the current state of the art, this step is recommended before the routine dilation of a patient's eye.

Second, the inventive composition is instilled into the eye in a manner similar to other currently available compositions for eye examination known by those skilled in the art.

Third, IOP is measured, preferably by applanation tonometry, which is permitted by the anesthetic and dye components contained in the composition. Additional instillation of the composition or of a dilating agent may be given after IOP is measured, if needed, to further enhance the speed or amplitude of pupillary dilation, according to clinical judgment (e.g., dark irises). IOP can also be measured using other techniques. For example, IOP can be measured by Schiotz tonometry, with a TONOPEN™ device, or by pnumotonomotry. However, with Schiotz tonometry and with the TONOPEN™ device, a dye is typically not necessary. Therefore, if IOP is measured according to these teachings, the inventive composition may not include a dye component, although the dye component would still be useful for disclosing ocular pathology.

Fourth, the clinician examines the optic nerve, and makes the appropriate entries and drawings in the patient's chart, as in any other routine eye examination. At this time, approximately fifteen minutes have elapsed.

The preferred inventive composition promotes rapid pupillary dilation by two mechanisms. First, because the preferred composition contains an anesthetic and preservative, the corneal epithelial permeability is increased, thereby increasing the absorption of the dilating agent. This increases the delivery of the dilating agent(s) to the ciliary muscle and promotes rapid and complete pupillary dilation. Second, the method of administering the inventive composition described above is more efficient than currently available compositions and procedures because pupillary dilation is initiated at an earlier stage of the examination with the inventive method (i.e., pupillary dilation is initiated before, rather than after IOP measurement). Thus, in most cases, the inventive method causes sufficient pupillary dilation for the clinician to perform dilated fundus examination without the inefficient waiting period, as is required with the current state of the art.

For illustrative purposes, the method of administering currently available agents according to the current state of the art (the "standard regimen") is compared to the preferred method using the preferred inventive composition below:

1. Standard Regimen (times shown for each step is approximate):

Slit lamp exam → anesthetic drop (#1) → fluorescein strip (#2) → IOP measurement
   (5 min.)              (2 min.)                 (2 min.)              (3 min.)
   → dilating drops (#3 & #4) → WAITING PERIOD → dilated fundus exam
                (3 min.)                 (20 min.)              (5 min.)
   Total Elapsed Time is approximately 40 minutes 2. Inventive Composition:

Slit lamp → inventive drop (#1) → IOP measurement → chart notes → dilated fundus exam
   (5 min.)        (2 min.)                (3 min.)          (5 min.)           (5 min.)
   Total Elapsed Time is approximately 20 minutes In summary, the inventive composition allows for the instillation of a single topical composition at or near the beginning of the eye examination (before the IOP measurement) which contains all the agents necessary to perform a complete eye examination. The composition, when administered in the method described herein, eliminates the inefficient waiting period (approximately twenty minutes) required in the current state of the art. Therefore, the composition maximizes efficiency, minimizes time and cost, and minimizes patient discomfort associated with instillation of multiple eye drops.

It is also possible, although not preferable, to administer some or all of the components of the inventive composition separately, rather than as a single combination. For example, the anesthetic, dye, and dilating agents can be administered separately and sequentially (in any order), but still all be instilled before IOP measurement. Administering the components in this manner allows the patient and clinician to avoid the waiting time associated with administering the dilating agent after measuring IOP. This method of administration may be preferred when using a method other than applanation tonometry to measure IOP because other methods do not require a dye, as discussed earlier. Therefore, a clinician could instill an anesthetic and a dilating agent separately, but before measuring IOP, rather than instilling the preferred combination drop. It is also possible to combine some, but not all of the components of the inventive composition and then apply this combination separately, but in conjunction with other components, all before measuring IOP.

It should also be appreciated that there are many other permutations for combining some or all of the components that comprise the inventive composition. For example, the anesthetic or dye, but not both, can be combined with a dilating agent.

Significantly, the inventive composition can have applications other than in the routine eye exam. For example, the inventive composition may be used before ophthalmic surgery. In this application, the inventive composition would both anesthetize the eye and dilate the pupil, thereby permitting many types of ophthalmic surgery, including cataract and retinal surgery. The dye component of the inventive composition would be useful to mark the operative eye, and prevent inadvertent operation on the fellow eye. Finally, the use of the inventive composition in this application before eye surgery would still minimize time for multiple instillations, minimize patient discomfort and maximize efficiency.

EXAMPLES

The following examples illustrate the usefulness and effectiveness of the compositions and methods of the present invention. In five clinical studies (A, B, C, D, and E) involving 10 patients in each study group, the testing composition was demonstrated to be efficacious for a complete eye examination. IOP measurement by applanation tonometry was accurate and not artifactually elevated in sample populations of both normal and glaucomatous patients. The composition was also shown to produce rapid, complete pupillary dilation for fundus examination without any additional waiting period after IOP measurement, as is required by the current state of the art.

Example 1

A first clinical study (Study A) was conducted on ten normal patients (cases A1–A10 below) to determine the approximate time an experienced clinician spent between initial instillation of the testing composition and applanation tonometry. The average time between initial instillation and initiating IOP measurement was 152.1 seconds, or 2 minutes, 32.1 seconds. The maximum time was 240 seconds or 4 minutes. (Case A10). Table 1 summarizes the results of Study A. The importance of this time measurement is discussed below after considering the results of Study B.

TABLE 1

(Study A)
CLINICAL EVALUATION OF TIME BETWEEN COMPOSITION
INSTILLATION & APPLANATION TONOMETRY

| CASE | TIME (sec.) |
|---|---|
| A1 | 125 |
| A2 | 63 |
| A3 | 189 |
| A4 | 204 |
| A5 | 79 |
| A6 | 110 |
| A7 | 145 |
| A8 | 156 |
| A9 | 210 |

TABLE 1-continued (Study A)
CLINICAL EVALUATION OF TIME BETWEEN COMPOSITION
INSTILLATION & APPLANATION TONOMETRY

| CASE | TIME (sec.) |
|---|---|
| A10 | 240 (maximum) |
| Mean | 152.1 = 2 min., 32.1 sec. |

Example 2

A second clinical study (Study B) was conducted on ten different normal patients (cases B1–B10 below) to measure the time between initial instillation of the composition and initial pupillary dilation. The average time was 306.8 seconds, or 5 minutes, 6.8 seconds. The minimum time was 250 seconds, or 4 minutes, 10 seconds. (Case B2). Thus, in every case, the time between initial instillation and initial pupillary dilation exceeded four minutes, the maximum time from initial instillation to completing IOP measurement. Table 2 summarizes the results of Study B.

TABLE 2

(Study B)
CLINICAL EVALUATION OF TIME FROM INITIAL
INSTILLATION TO INITIAL PUPILLARY DILATION

| CASE | TIME (sec.) |
|---|---|
| B1 | 305 |
| B2 | 250 (minimum) |
| B3 | 263 |
| B4 | 279 |
| B5 | 363 |
| B6 | 377 |
| B7 | 354 |
| B8 | 280 |
| B9 | 287 |
| B10 | 310 |
| Mean | 306.8 = 5 min., 6.8 sec. |

Summarizing the results from Study A and Study B, the time between initial instillation of the preferred composition and applanation tonometry was, in all cases, less than the time to initial pupillary dilation. This is important because it is thought that pupillary dilation can artifactually elevate IOP as measured by applanation tonometry. Thus, Studies A and B show that IOP measurement should not be artifactually elevated after instilling the inventive composition since IOP measurement can be performed before any measurable pupillary dilation occurs.

Example 3

A third clinical study (Study C) was conducted on ten different patients (cases C1–C10 below) to compare IOP measurement following use of the inventive composition with IOP measurement using the state of the art compositions ("standard regimen"). The study population consisted of a group of normal, non-glaucomatous patents with equal intraocular pressures in both eyes on a previous exam, who were not on any topical medications, and who did not have any prior ophthalmic surgery. The testing composition was instilled to one eye of each member of the study group (test eye) and a commercially available solution of fluorescein sodium (0.25%) and benoxinate hydrochloride (0.4%), was applied to the other eye (control eye—standard regimen). Both eyes were then examined and applanation tonometry performed. The average IOP measured 16.5 mm Hg in the test eyes and 16.1 mm Hg in the control eyes. This difference is not clinically significant (p>0.10). Further, the difference between measured IOP in the test eye and the control eye was equal to or less than 2 mm Hg in all cases, within the range of measurement error in routine clinical practice. Table 3 summarizes the results of this third study.

TABLE 3

(Study C)
CLINICAL COMPARISON OF IOP MEASUREMENT FOLLOWING USE OF TESTING COMPOSITION VS. STANDARD REGIMEN

| CASE | IOP-PREFERRED-COMPOSITION (mm Hg) | IOP-STANDARD REGIMEN (mm Hg) | DIFF. |
|---|---|---|---|
| C1 | 13 | 14 | −1 |
| C2 | 12 | 11 | +1 |
| C3 | 15 | 15 | 0 |
| C4 | 17 | 16 | +1 |
| C5 | 19 | 21 | −2 |
| C6 | 20 | 18 | +2 |
| C7 | 13 | 12 | +1 |
| C8 | 16 | 15 | +1 |
| C9 | 19 | 18 | +1 |
| C10 | 21 | 21 | 0 |
| MEAN | 16.5 | 16.1 | +0.4 |

Summarizing the results from the third study, in a population of normal subjects, measurement of IOP by applanation tonometry did not significantly differ when the testing composition was used, as compared with the current state of the art composition.

Example 4

A fourth clinical study (Study D) was conducted on ten different patients (cases D1–D10 below) to confirm the findings in Study C, but in a group of glaucomatous patients. The study population consisted of a group of glaucomatous patients, who did not have any prior ophthalmic surgery, who were on identical topical glaucoma medications in both eyes, and who had equal intraocular pressure in both eyes on the previous exam. The testing composition was instilled in the right (test) eye and a solution of fluorescein sodium (0.25%) and benoxinate hydrochloride (0.4%), was instilled in the left eye (control eye—standard regimen). Both eyes were then examined, and IOP measured by intraocular tonometry. The average IOP measured 18.0 mm Hg in the test eyes, and 18.1 mm Hg in the control eyes. This difference is not clinically significant (p>0.10). The difference between IOP in the test and control eyes was equal to or less than 2 mm Hg in all cases, which is within the range of measurement error in routine clinical practice. Table 4 summarizes the results of Study D.

TABLE 4

(Study D)
CLINICAL COMPARISON OF IOP MEASUREMENT IN GLAUCOMA PATIENTS FOLLOWING USE OF TESTING COMPOSITION VS. STANDARD REGIMEN

| CASE | IOP-TESTING-COMPOSITION (mm Hg) | IOP-STANDARD REGIMEN (mm Hg) | DIFF. (mm Hg) |
|---|---|---|---|
| D1 | 22 | 23 | −1 |
| D2 | 24 | 24 | 0 |
| D3 | 19 | 18 | +1 |
| D4 | 17 | 16 | +1 |
| D5 | 8 | 9 | −1 |
| D6 | 17 | 16 | +1 |
| D7 | 20 | 22 | −2 |
| D8 | 26 | 25 | +1 |
| D9 | 9 | 10 | −1 |
| D10 | 18 | 18 | 0 |
| MEAN | 16.0 | 18.1 | −0.1 |

Thus, in a population of glaucomatous subjects, measurement of IOP by applanation tonometry using the testing composition did not differ significantly compared to using the state of the art composition.

Example 5

A fifth clinical study (Study E) was performed on ten different patients (cases E1–E10 below) to determine the adequacy of pupillary dilation for performing dilated fundus exam when using the inventive composition as compared to using currently available compositions according to the current state of the art ("standard regimen"). The study population consisted of a group of normal subjects not on topical medications, who had no prior ophthalmic surgery, and who had normal, symmetric pupils. First, both eyes were examined by slit lamp. The testing composition was then instilled in the right (test) eye and a solution of fluorescein sodium (0.25%) and benoxinate hydrochloride (0.4%) was instilled in the left eye (control eye—standard regimen). Next, IOP was measured in both eyes by intraocular tonometry. In the control eye, as per the state of the art procedure, after measuring IOP, dilating agents phenylephrine (5%) and tropicamide (1%) were then instilled. Nothing additional was instilled in the test eye after measuring IOP. Typical notes and drawings of the examination were then recorded in the patient's chart. At this time, approximately ten to fifteen minutes elapsed since the initial instillation in both eyes. Pupillary diameter in both eyes was measured and dilated fundus exam was then attempted in both the test (right) and the control (left) eyes. The design of Study E is outlined diagrammatically below:

1. Testing Composition: Right Eye:

Slit lamp exam → testing composition drop → IOP measurement → chart notes → pupil measurement → dilated fundus exam attempted -continued 2. Standard Regimen: Left Eye:

Slit lamp exam → anesthetic drop → fluorescein strip → IOP measurement → dilating drops → chart notes → pupil measurement → dilated fundus exam attempted The results of the study are as follows: dilated fundus examination of both the test and control eyes was attempted at an average of 661.1 seconds (11 minutes, 1.1 seconds) after the testing composition was initially instilled. When attempting to perform the dilated fundus examination on the test eyes, pupillary dilation averaged 8.8 mm and was sufficient for a complete peripheral fundus examination in 100% of the cases (10 of 10 test eyes). In contrast, pupillary dilation in the control eyes averaged only 6.85 mm at the same time that the test eyes averaged 8.8 mm, and was sufficient for a complete peripheral fundus examination in only 60% of cases (6 of 10 control eyes). Thus, in 4 of the 10 cases, the patient and clinician had to wait longer with the standard regimen and method of administration to achieve sufficient pupillary dilation to permit the fundus examination. Table 5 summarizes the results of Study E.

can be reduced and even eliminated in most cases. Additionally, cost savings can be realized because multiple agents do not have to be stocked.

An embodiment of the inventive composition can also be used to replace the current state of the art regimen of drops before many types of ophthalmic surgery, including cataract extraction. For example, prior to the surgery, the clinician can instill the composition that includes the anesthetic, the dilating agent, and the dye. In this application, the anesthetic component of the invention composition would reduce the pain from the dilating agent(s), the dilating agent(s) would dilate the pupil to permit intraocular surgery, and the dye component would mark the surgical eye pre-operatively, thereby reducing the chance of inadvertent surgery on a healthy fellow eye. Again, with this application, patient discomfort from multiple drop instillations is minimized,

TABLE 5

(Study E)
CLINICAL COMPARISON OF PUPILLARY DILATION:
TESTING COMPOSITION VS. STANDARD REGIMEN

| CASE | TIME (sec.) | PUPIL DIAMETER USING TEST COMPOSITION (mm) | SUFFICIENT DILATION FOR FUNDUS EXAM? | DIAMETER USING STANDARD REGIMEN | SUFFICIENT DILATION FOR FUNDUS EXAM? |
|---|---|---|---|---|---|
| E1 | 605 | 8.0 | Y | 6.0 | N* |
| E2 | 590 | 8.5 | Y | 6.0 | N* |
| E3 | 619 | 9.0 | Y | 6.0 | N* |
| E4 | 715 | 8.5 | Y | 7.0 | Y |
| E5 | 703 | 9.5 | Y | 6.5 | Y |
| E6 | 710 | 9.0 | Y | 8.0 | Y |
| E7 | 610 | 9.5 | Y | 6.0 | N* |
| E8 | 654 | 9.0 | Y | 7.0 | Y |
| E9 | 675 | 8.0 | Y | 7.5 | Y |
| E10 | 720 | 9.0 | Y | 8.5 | Y |
| MEAN | 661.1 = 11 min., 1.1 sec. | 8.8 | 10 of 10 with testing composition | 6.9 | 6 of 10 with standard regimen |

*Required additional waiting time to perform dilated fundus exam.

Thus, in a population of normal subjects, pupillary dilation was greater after the same amount of elapsed time from the beginning of the eye exam using the testing composition according to the prescribed method of administration than using currently available agents according to the current state of the art in all cases. Moreover, a complete dilated fundus examination could be performed without an additional waiting period in 100% of cases using the preferred composition, compared to only 60% of the cases using currently available agents according to the current state of the art.

Based on the above studies involving both normal and glaucomatous patients, the inventive composition was demonstrated to be efficacious in allowing complete eye examination, including accurate IOP measurement (ie., without artifactually elevating IOP measurement). By containing all the necessary agents for a complete exam, the number of topical instillations is minimized, thereby minimizing patient discomfort. The examination is more time efficient, because multiple drops are not instilled, and because the waiting period for sufficient pupillary dilation efficiency is maximized, rapid and complete dilation is promoted, and cost savings are realized by not having to stock multiple drops.

While the invention has been shown and described herein with reference to particular embodiments, it is to be understood that various additions, substitutions, or modifications of form, arrangement, proportions, components, methods of administration, and otherwise, used in the practice of the invention and which are particularly adapted to specific environments and operative requirements, may be made to the described embodiment without departing from the spirit and scope of the present invention.

I claim:

1. An ophthalmic composition comprising a solution mixture of diagnostically acceptable amounts of a local topical anesthetic and a pupillary dilating agent.

2. The composition according to claim 1, wherein the anesthetic is proparacaine, tetracaine, lidocaine, procaine, hexylcaine, cocaine, bupivicaine, benoxinate, mepivacaine, prilocaine, etidocaine, benzocaine, chloroprocaine, propoxycaine, dyclonin, dibucaine, pramoxine, or oxybuprocaine.

3. The composition according to claim 2, wherein the anesthetic is present in an amount of about 0.01% to about 10%.

4. The composition according to claim 1, wherein the pupillary dilating agent is a sympathomemetic agent or a parasympatholytic agent and is present in an amount of about 0.01% to about 15%.

5. The composition according to claim 1, wherein the pupillary dilating agent is phenylephrine, tropicamide, cyclopentolate, hydroxyamphetamine, atropine, or homatropine and is present in an amount of about 0.1% to about 10%.

6. The composition according to claim 1, further comprising a diagnostically acceptable amount of a dye.

7. The composition according to claim 6, wherein the dye is fluorescein, rose bengal, or lissamine green and is present in an amount of about 0.01% to about 10%.

8. The composition according to claim 1, further including a diagnostically acceptable amount of a preservative.

9. The composition according to claim 8, wherein the preservative is benzalkonium chloride in an amount of about 0.0001% to about 0.1%, chlorobutanol in an amount of about 0.1% to about 10%, polysorbate 20 in an amount of about 0.0001% to about 10%, EDTA in an amount of about 0.0001% to about 10%, methylparaben and propylparaben in an amount of about 0.0001% to about 10%, phenylethyl alcohol in an amount of about 0.0001% to about 10%, chlorhexidine in an amount of about 0.0001% to about 10%, or polyaminopropyl biguanide in an amount of about 0.0001% to about 10%.

10. The composition according to claim 1, further including a diagnostically acceptable amount of a wetting agent and a diluting agent.

11. The composition according to claim 10, wherein the wetting agent is carboxymethylcellulose, hydroxypropyl methylcellulose, glycerin, mannitol, polyvinyl alcohol or hydroxyethylcellulose and the diluting agent is water, distilled water, sterile water, or artificial tears, wherein the wetting agent is present in an amount of about 0.001% to about 10%.

12. The composition according to claim 1, further including a diagnostically acceptable amount of a buffer to adjust the pH of the solution between about 4.0 to about 7.5.

13. An ophthalmic composition comprising a diagnostically acceptable amount of a topical local anesthetic, and a pupillary dilating agent, wherein the composition is an ointment, cream, or gel.

14. An ophthalmic composition comprising a solution mixture of diagnostically acceptable amounts of a dye and a pupillary dilating agent.

15. The composition according to claim 14, wherein the dye is fluorescein, rose bengal, or lissamine green in an amount of about 0.01% to about 10%, and the dilating agent is a sympathomemetic agent or a parasympatholytic agent in an amount of about 0.01% to about 15%.

16. The composition according to claim 15, wherein the dilating agent is phenylephrine, tropicamide, cyclopentolate, hydroxyamphetamine, atropine, or homatropine and is present in an amount of about 0.1% to about 10%.

17. The composition according to claim 14, further comprising a diagnostically acceptable amount of a preservative.

18. The composition according to claim 17, wherein the preservative is benzalkonium chloride in an amount of about 0.0001% to about 0.1%, chlorobutanol in an amount of about 0.1% to about 10%, polysorbate 20 in an amount of about 0.0001% to about 10%, EDTA in an amount of about 0.0001% to about 10%, methylparaben and propylparaben in an amount of about 0.0001% to about 10%, phenylethyl alcohol in an amount of about 0.0001% to about 10%, chlorhexidine in an amount of about 0.0001% to about 10%, or polyaminopropyl biguanide in an amount of about 0.0001% to about 10%.

19. The composition according to claim 14, further comprising a diagnostically acceptable amount of a wetting agent and a diluting agent.

20. The composition according to claim 19, wherein the wetting agent is carboxymethylcellulose, hydroxypropyl methylcellulose, glycerin, mannitol, polyvinyl alcohol or hydroxyethylcellulose and the diluting agent is water, distilled water, sterile water, or artificial tears, wherein the wetting agent is present in an amount of about 0.001% to about 10%.

21. The composition according to claim 19, further comprising a diagnostically acceptable amount of a topical local anesthetic and a preservative.

22. The composition according to claim 21, wherein the anesthetic is proparacaine, tetracaine, lidocaine, procaine, hexylcaine, cocaine, bupivicaine, benoxinate, mepivacaine, prilocaine, etidocaine, benzocaine, chloroprocaine, propoxycaine, dyclonin, dibucaine, pramoxine, or oxybuprocaine and is present in an amount of about 0.1% to about 5%, the dye is fluorescein, rose bengal, or lissamine green and is present in an amount of about 0.05% to about 5%, the dilating agent is phenylephrine, tropicamide, cyclopentolate, hydroxyamphetamine, atropine, or homatropine and is present in an amount of about 0.1% to about 10%, the wetting agent is hydroxypropyl methylcellulose and is present in an amount of about 0.1% to about 1%, the preservative is benzalkonium chloride in an amount of about 0.0001% to about 0.1% or chlorobutanol in an amount of about 0.1% to about 10%, and the diluting agent is sterile water.

23. The composition according to claim 21, wherein the anesthetic is proparacaine or tetracaine and is present in an amount of about 0.1% to about 1%, the dilating agent is phenylephrine or tropicamide and is present in an amount of about 0.1% to about 5%, the dye is fluorescein and is present in an amount of about 0.1% to about 1%, the wetting agent is hydroxypropyl methylcellulose and is present in an amount of about 0.1% to about 1%, the preservative is benzalkonium chloride in an amount of about 0.0001% to about 0.1% or chlorobutanol in an amount of about 0.1% to about 10%, and the diluting agent is sterile water.

24. A method of conducting an eye examination comprising the steps of:

applying a topical local anesthetic and a dilating agent in combination to the eye;

measuring intraocular pressure of the eye after the applying step; and conducting a dilated fundus examination after the measuring step.

25. The method of claim 24, wherein the anesthetic and the dilating agent are applied together from a single solution mixture.

26. The method of claim 24, wherein the step of applying further includes applying a dye to the eye, wherein the anesthetic, the dilating agent and the dye are applied together from a single solution mixture.

27. The method of claim 24, wherein the measuring step is performed by applanation tonometry.

28. A method of treating an eye prior to surgery, comprising the step of applying a topical local anesthetic and a dilating agent to the eye, wherein the anesthetic and the dilating agent are applied together from a single solution mixture.

29. The method of claim 28, wherein the step of applying further includes applying a dye to the eye, wherein the dye, the dilating agent, and the anesthetic are applied together from a single solution mixture.

* * * * *